US006861253B2

(12) United States Patent
Brasseur et al.

(10) Patent No.: US 6,861,253 B2
(45) Date of Patent: Mar. 1, 2005

(54) POLYPEPTIDE INDUCING ANTIBODIES NEUTRALIZING HIV

(75) Inventors: Robert Brasseur, Haillot (BE); Benoit Charloteaux, Namur (BE); Michel Chevalier, Beaurepaire (FR); Raphaelle El Habib, Chaponost (FR); Tino Krell, Ecully (FR); Regis Sodoyer, Sainte Foy les Lyon (FR)

(73) Assignee: Aventis Pasteur S.A., Lyon Cedex (FR)

( * ) Notice: Subject to any disclaimer, the term of this patent is extended or adjusted under 35 U.S.C. 154(b) by 239 days.

(21) Appl. No.: 10/040,349

(22) Filed: Jan. 7, 2002

(65) Prior Publication Data

US 2003/0082521 A1 May 1, 2003

Related U.S. Application Data

(60) Provisional application No. 60/267,165, filed on Feb. 7, 2001.

(51) Int. Cl.[7] ............................................. C12N 15/00
(52) U.S. Cl. ...................... 435/320.1; 435/5; 435/325; 536/23.72; 530/324; 530/350; 530/826; 424/188.1; 424/193.1; 424/208.1; 424/200.1
(58) Field of Search ....................... 435/5, 320.1, 325; 536/23.72; 530/324, 350, 826; 424/188.1, 193.1, 208.1, 200

(56) References Cited

FOREIGN PATENT DOCUMENTS

| WO | WO 00 08167 | 2/2000 | ................... 15/49 |
|----|-------------|--------|--------------------------|
| WO | WO 00 40616 | 7/2000 | |
| WO | WO 01 44286 | 6/2001 | |
| WO | WO 01 70262 | 9/2001 | ................... 39/12 |

OTHER PUBLICATIONS

Shu, et al., "Helical Interactions in the HIV–1 gp41 Core Reveal Structural Basis for the Inhibitory Activity of gp41 Peptides," Biochemistry 2000, 39, 1634–1642.
Louis, et al., "Design and Properties of $N_{CCG}$–gp41, a Chimeric gp41 Molecule with Nanomolar HIV Fusion Inhibitory Activity," vol. 276, No. 31, Issue of Aug. 3, pp. 29485–29489, 2001.
Wingfield, et al., "The extracellular Domain of Immunodeficiency Virus gp41 Protein: Expression in *Escherichia coli*, Purification, and Crystallization," Protein Science (1997), 6:1653–1660, Cambridge University Press.

DeRosny, et al., "Peptides Corresponding to the Heptad Repeat Motifs in the Transmembrane Protein (gp41) of Human Immunodeficiency Virus Type 1 Elicit Antibodies of Receptor–Activated Conformations of the Envelope Glycoprotein," Journal of Virology, Sep. 2001, pp. 8859–8863.

Yang, et al., "The Crystal Structure of the SIV gp41 Ectodomain at 1.47 A Resolution," Journal of Structural Biology, 126, 131–144 (1999).

Caffrey, et al., "Three–Dimensional Solution Structure of the 44 kDa Ectodomain of SIV gp41," The EMBO Journal vol. 17, No. 16, pp. 4572–4584, 1998.

Weng, Yongkai and Weiss, Carol D., "Mutational Analysis of Residues in the Coiled–Coil Domain of Human Immunofeficiency Virus Type 1 Transmembrane Protein gp41," Journal of Virology, Dec. 1998, pp. 9676–9682.

Cao, et al., "Effects of Amino Acid Changes in the Extracellular Domain of the Human Immunodeficiency Virus Type 1 gp41 Envelope Glycoprotein," Journal of Virology, May 1993, pp. 2747–2755.

Weng, et al., "Structure–Function Studies of the Self–Assembly Domain of the Human Immunodficiency Virus Type 1 Transmembrane Protein gp41," Journal of Virology, Jun. 2000, pp. 5368–5372.

LaCasse, et al., "Fusion–Competent Vaccines: Broad Neutralization of Primary Isolates of HIV," Research Articles, Jan. 15, 1999 vol. 383.

Weissenhorn, et al., "Atomic Structure of the Ectodomain from HIV–1 gp41," Nature, vol. 387, May 1997.

Malashkevich, et al., "Crystal Structure of the Simian Immunodeficiency Virus (SIV) gp41 core: Conserved Helical Interactions Underlie the Broad Inhibitory Activity of gp41 Peptides," Proc. Natl. Acad. Sci. USA vol. 95, pp. 9134–9139, Aug. 1998 Biochemistry.

Montefiori, David C. and Evans, Thomas G., "Toward an HIV Type 1 Vaccine that Generates Potent, Broadly Cross–Reactive Neutralizing Antibodies," Aids Research and Human Retroviruses, vol. 15, No. 8, 1999, pp. 689–698.

*Primary Examiner*—Jeffrey Stucker
(74) *Attorney, Agent, or Firm*—McDonnell Boehnen Hulbert & Berghoff

(57) ABSTRACT

The present invention thus provides a polypeptide capable of forming a structure corresponding to or mimicking the intermediate of gp41 as well as its use in a vaccine for treating or preventing HIV infections.

16 Claims, 4 Drawing Sheets

Figure 1:
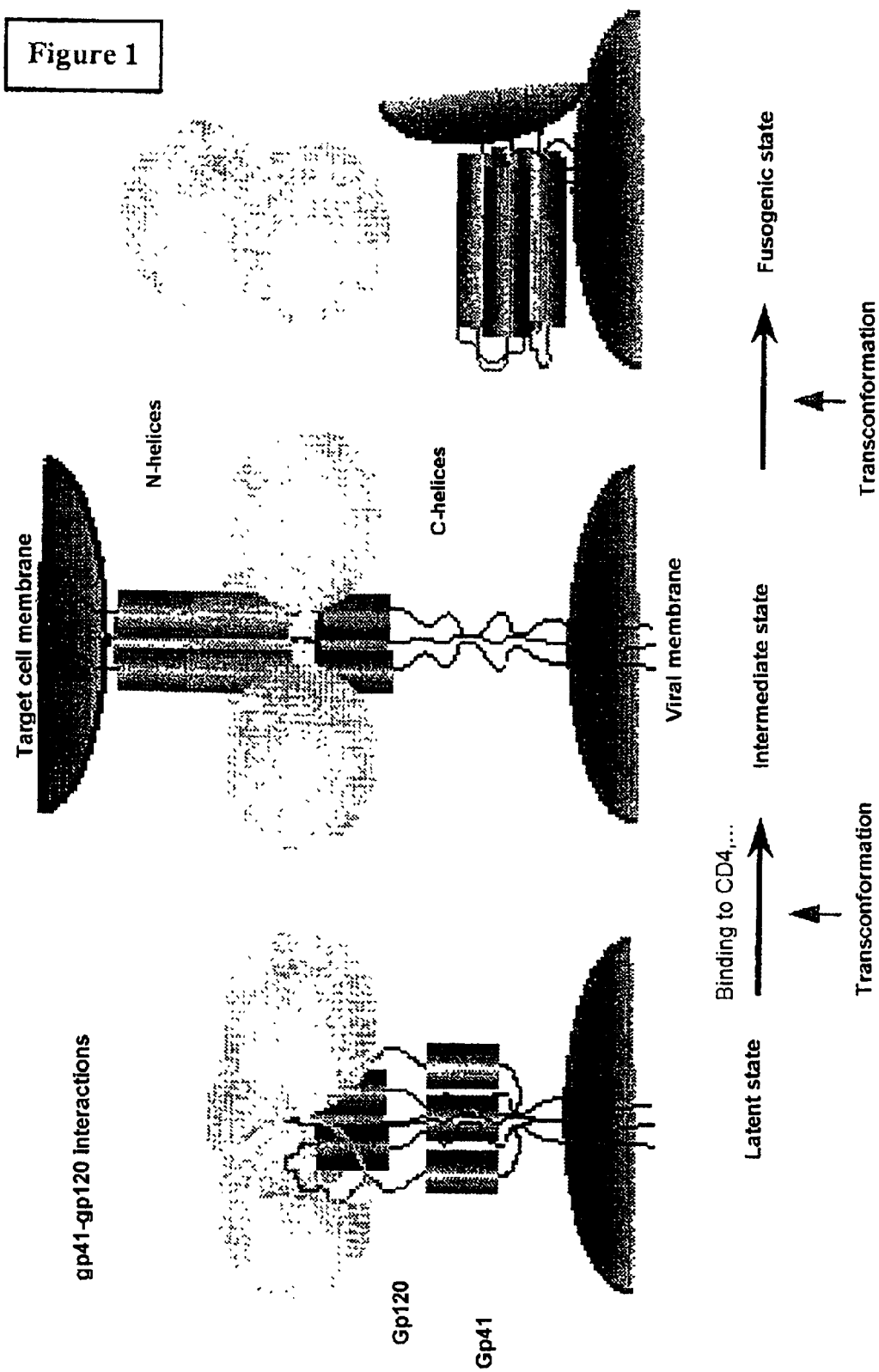

Figure 2: Complete sequence of the gp41 LAI protein

<u>avgigalfl gflgaagstm gaas</u>mtltvq arqllsgivq qqnnllraie 49 aqqhllqltv wgikqlqari laverylkdq qllgiwgcsg klicttavpw 99 naswsnksle qiwnnmtwme wdreinnyts lihslieesq nqqekneqel 149 leldkwaslw nwfnitnwlw yiklfimivg glvglrivfa vlsivnrvrq 199 gysplsfqth lptprgpdrp egieeegger drdrsirlvn gslaliwddl 249 rslclfsyhr lrdlllivtr ivellgrrcw ealkywwnll qvwselknsa 299 vsllnataia vaegtdrvie vvqgacrair hiprrirqgl erill 344

\_\_\_\_\_ : Fusion peptide (AA 1-23)
----- : Transmembrane domain (AA173-194)

Figure 3: Sequence of the polypeptide which derives from the gp41 LAI protein used as the starting product in the examples.

```
     mtltvq arqllsgivq qqnnllraie aqqhllqltv wgikqlqari  46
laverylkdq qllgiwgcsg klicttavpw naswsnksle qiwnnmtwme  96
wdreinnyts lihslieesq nqqekneqel leldkwaslw nwfnitnwlw 146
yiknrvrqgy splsfqthlp tprgpdrpeg i                     177
```

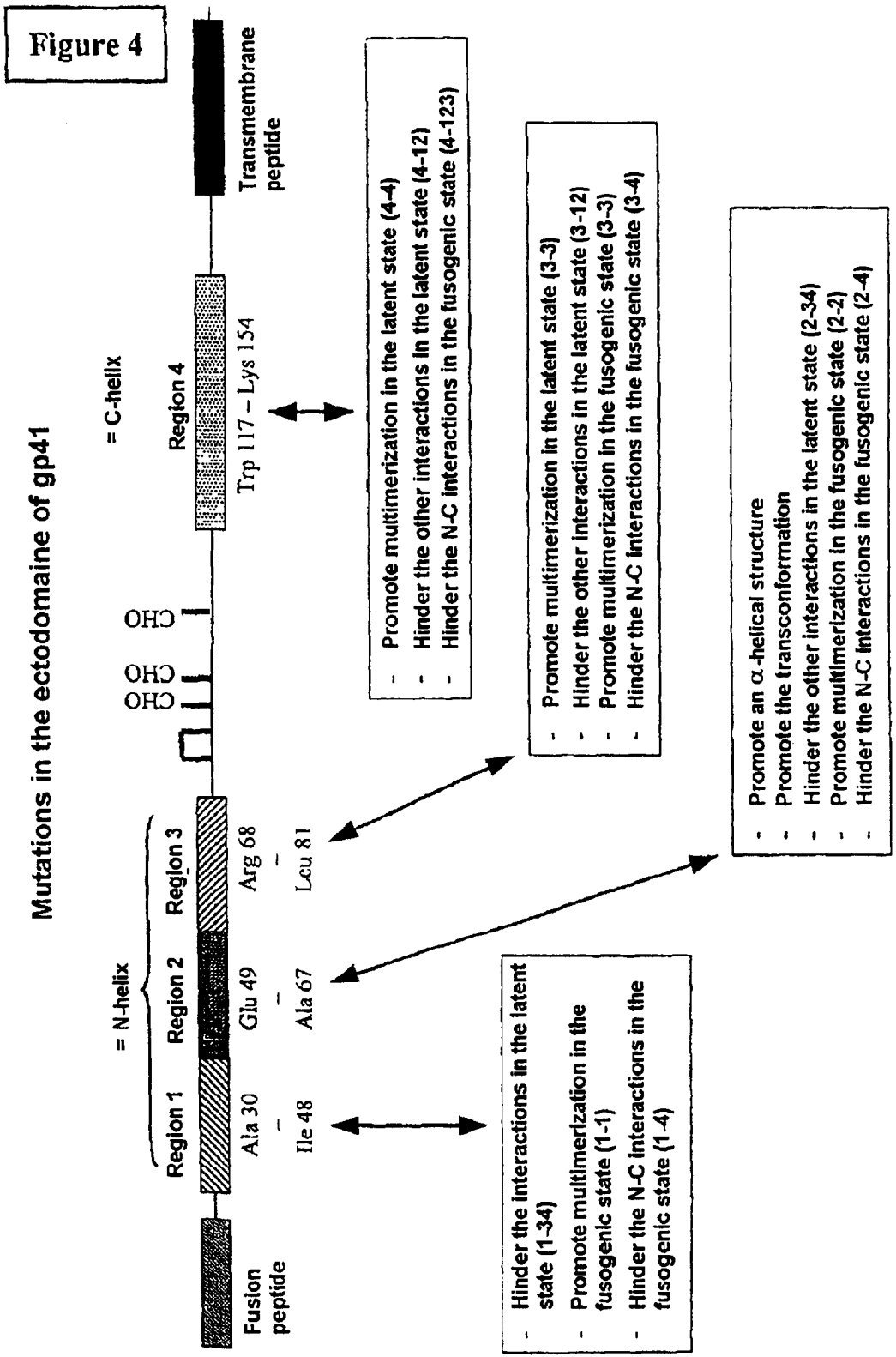

SEQUENCE LISTING

<160> NUMBER OF SEQ ID NOS: 2

<210> SEQ ID NO 1
<211> LENGTH: 344
<212> TYPE: PRT
<213> ORGANISM: Human immunodeficiency virus type 1
<220> FEATURE:
<221> NAME/KEY: Peptide
<222> LOCATION: (1)..(344)
<223> OTHER INFORMATION: gp41 LAI protein

<400> SEQUENCE: 1

```
Ala Val Gly Ile Gly Ala Leu Phe Leu Gly Phe Leu Gly Ala Ala Gly
1               5                   10                  15

Ser Thr Met Gly Ala Ala Ser Met Thr Leu Thr Val Gln Ala Arg Gln
            20                  25                  30

Leu Leu Ser Gly Ile Val Gln Gln Gln Asn Asn Leu Leu Arg Ala Ile
        35                  40                  45

Glu Ala Gln Gln His Leu Leu Gln Leu Thr Val Trp Gly Ile Lys Gln
    50                  55                  60

Leu Gln Ala Arg Ile Leu Ala Val Glu Arg Tyr Leu Lys Asp Gln Gln
65                  70                  75                  80

Leu Leu Gly Ile Trp Gly Cys Ser Gly Lys Leu Ile Cys Thr Thr Ala
                85                  90                  95

Val Pro Trp Asn Ala Ser Trp Ser Asn Lys Ser Leu Glu Gln Ile Trp
            100                 105                 110

Asn His Thr Thr Trp Met Glu Trp Asp Arg Glu Ile Asn Asn Tyr Thr
        115                 120                 125

Ser Leu Ile His Ser Leu Ile Glu Glu Ser Gln Asn Gln Gln Glu Lys
    130                 135                 140

Asn Glu Gln Glu Leu Leu Glu Leu Asp Lys Trp Ala Ser Leu Trp Asn
145                 150                 155                 160

Trp Phe Asn Ile Thr Asn Trp Leu Trp Tyr Ile Lys Leu Phe Ile Met
                165                 170                 175

Ile Val Gly Gly Leu Val Gly Leu Arg Ile Val Phe Ala Val Leu Ser
            180                 185                 190
```

-continued

```
Ile Val Asn Arg Val Arg Gln Gly Tyr Ser Pro Leu Ser Phe Gln Thr
            195                 200                 205

His Leu Pro Thr Pro Arg Gly Pro Asp Arg Pro Glu Gly Ile Glu Glu
        210                 215                 220

Glu Gly Gly Glu Arg Asp Arg Asp Arg Ser Ile Arg Leu Val Asn Gly
225                 230                 235                 240

Ser Leu Ala Leu Ile Trp Asp Asp Leu Arg Ser Leu Cys Leu Phe Ser
                245                 250                 255

Tyr His Arg Leu Arg Asp Leu Leu Leu Ile Val Thr Arg Ile Val Glu
                260                 265                 270

Leu Leu Gly Arg Arg Cys Trp Glu Ala Leu Lys Tyr Trp Trp Asn Leu
            275                 280                 285

Leu Gln Val Trp Ser Glu Leu Lys Asn Ser Ala Val Ser Leu Leu Asn
            290                 295                 300

Ala Thr Ala Ile Ala Val Ala Glu Gly Thr Asp Arg Val Ile Glu Val
305                 310                 315                 320

Val Gln Gly Ala Cys Arg Ala Ile Arg His Ile Pro Arg Arg Ile Arg
                325                 330                 335

Gln Gly Leu Glu Arg Ile Leu Leu
            340

<210> SEQ ID NO 2
<211> LENGTH: 177
<212> TYPE: PRT
<213> ORGANISM: Human immunodeficiency virus type 1
<220> FEATURE:
<221> NAME/KEY: Peptide
<222> LOCATION: (1)..(177)
<223> OTHER INFORMATION: polypeptide derived from gp41 LAI

<400> SEQUENCE: 2

Met Thr Leu Thr Val Gln Ala Arg Gln Leu Leu Ser Gly Ile Val Gln
1               5                   10                  15

Gln Gln Asn Asn Leu Leu Arg Ala Ile Glu Ala Gln Gln His Leu Leu
            20                  25                  30

Gln Leu Thr Val Trp Gly Ile Lys Gln Leu Gln Ala Arg Ile Leu Ala
        35                  40                  45

Val Glu Arg Tyr Leu Lys Asp Gln Gln Leu Leu Gly Ile Trp Gly Cys
    50                  55                  60

Ser Gly Lys Leu Ile Cys Thr Thr Ala Val Pro Trp Asn Ala Ser Trp
65              70                  75                  80

Ser Asn Lys Ser Leu Glu Gln Ile Trp Asn Asn Met Thr Trp Met Glu
                85                  90                  95

Trp Asp Arg Glu Ile Asn Asn Tyr Thr Ser Leu Ile His Ser Leu Ile
            100                 105                 110

Glu Glu Ser Gln Asn Gln Gln Glu Lys Asn Glu Gln Glu Leu Leu Glu
        115                 120                 125

Leu Asp Lys Trp Ala Ser Leu Trp Asn Trp Phe Asn Ile Thr Asn Trp
    130                 135                 140

Leu Trp Tyr Ile Lys Asn Arg Val Arg Gln Gly Tyr Ser Pro Leu Ser
145                 150                 155                 160

Phe Gln Thr His Leu Pro Thr Pro Arg Gly Pro Asp Arg Pro Glu Gly
                165                 170                 175

Ile
```

POLYPEPTIDE INDUCING ANTIBODIES NEUTRALIZING HIV

This application claims the benefit of U.S. Provisional Application No. 60/267,165, filed Feb. 7, 2001.

The present invention relates to a mutated polypeptide which derives from the gp41 protein, and also to a vaccine comprising it.

The development of a method for immunizing against HIV is, today, one of the priorities of scientific research.

The major obstacles represented by the great genetic variability of the virus and the poor exposure, to the immune system, of neutralizing viral epitopes considerably slow down the production of neutralizing immunity.

The HIV envelope glycoprotein which is required in order to confer on the virus its infectious nature represents the target for neutralizing antibodies. These characteristics have made the latter a subject of intense investigation.

The glycoprotein envelope (ENV) of the human immunodeficiency virus-1 (HIV-1) is synthesized from the gp160 precursor which, under the action of a protease, gives the gp120 and gp41 subunits.

The attachment of gp120/gp41 to the cellular receptors (CD4 or a receptor for chemokines, such as CCR5 or CXCR-4) induces a change of conformation of gp41 from a latent state (nonfusogenic) to a fusion-active state (fusogenic). Between these two states, a transient, termed "intermediate", state exists, during which gp41 has the appearance of a trans-membrane protein in both the viral and cell membranes (Weissenhorn et al Nature (1997), 387 (6631), 426–30).

Binding experiments have made it possible to establish that the nonfusogenic latent state is characterized by the inaccessibility of large portions of the ectodomaine of gp41. gp120 in fact interacts in such a way as to mask the epitopes. It has, moreover, been shown that the inhibition of the structural change from the intermediate state toward the fusogenic state by peptides used as competitors can affect viral infection (Weissenhorn W. et al, Molecular Membrane Biology, 1999, 16, 3–9).

The use of the fusogenic state of gp41 for immunization purposes is disclosed in WO 00/140616. According to that application, N-helices can be used alone or in combination with C-helices in order to reproduce, in the latter case, the fusogenic conformation of gp41.

The applicant provides a novel immunization antigen which can be used in immunization against HIV. The applicant has, in fact, demonstrated, for the first time, that the intermediate state of gp41 is capable of inducing antibodies which neutralize primary isolates of HIV.

The present invention therefore relates to a polypeptide capable of forming a structure corresponding to or mimicking the intermediate state of gp41 comprising at least one mutation selected in the group consisting of T35I or L; W49I or L; Q56I or L; I101D or S; I108D and W94D.

Acording to one particular embodiment, the polypeptide comprises at least another mutation selected in the group comprising the following mutations: G13A, L, M, I, W or K; Q17A or E; Q18A or E; A24Q, E, S or R; Q28A; T35I or L; V36Q or E; W37S or D; G38A, V, L, I, M or E; Q39A, V, L, I, M or E; K40E, A, V, L, I or M; Q41A, V, L, I, M or E; Q43A, V, L, I, M or E; L47A or D; V49I or L; R51A, N or E; Q56I; C64S; C70S; or L; W94D; D98A, V, L, I, M or K; R99A, N or E; I101D or S; Y104M or E; I108D; Q119A, V, L, I, M, S, N or R; E120A; K121A; E123A; E125A; R153N or A et R173N or A.

According to prefered embodiment, the polypeptide of the present invention comprises the following mutations: T35I; I101D; T35I+Q28I+I101D; T35I+Q28I+I101D+Q119N; I101D+I108D+Q131N+W37A; I101D+I108D+Q142N+L126D; W37A+I101D+I108D+Q119N or I101D+I108D+Q119N+L126D.

According to another aspect, the present invention relates to a conjugate comprising a polypeptide according to the invention conjugated to a carrier protein or peptide.

According to another aspect, the present invention relates to a DNA sequence encoding a polypeptide according to the invention or encoding a conjugate according to the invention.

The present invention also relates to an expression vector comprising said DNA sequence, and also to a host cell containing said vector.

A subject of the present invention is also a vaccine against HIV, comprising at least one polypeptide as defined above, at least one conjugate as defined above or at least one expression vector as defined above, a pharmaceutically acceptable support and, optionally, an adjuvant.

A subject of the present invention is also a method of induction of antibodies neutralizing HIV comprising administration to mamal of an efficient amount of a polypeptide of the invention.

Another subject of the present invention relates to the process for preparing a polypeptide as defined above, comprising the expression of said polypeptide using a host cell as defined above.

The invention is described in greater detail in the description which follows.

The phenomenon of conformational change in gp41 preceding the fusion of cell and viral membranes is illustrated in FIG. 1.

The applicant has demonstrated, surprisingly, that the intermediate state of gp41 induces antibodies which neutralize primary isolates of HIV. Induction of antibodies which neutralize primary isolates can be easily determined using the neutralization assay as described in the article by C. Moog et al (AIDS Research and human retroviruses, vol. 13(1), 13–27, 1997). In the context of the present invention, it is considered that neutralizing antibodies have been induced by the antigen assayed when the serum diluted to $\frac{1}{5}^{th}$ causes a 10-fold decrease in the amount of p24 present in the culture supernatant. The present polypeptide is thus particularly appropriate as a vaccine antigen usable for treatment and prevention of an HIV infection.

In the context of the present invention, the expression "polypeptide corresponding or mimicking the intermediate state of gp41" is intended to mean a polypeptide, preferably a trimeric polypeptide, which, under physiological conditions, has an open conformation. In this open conformation, at least one of the C-helices is not paired around the N-helices in the anti-paralleled orientation as present in the fusogenic form. Preferably, the three C-helices are not paired with the N-helices in the anti-parallel orientation as present in the fusogenic form. In such a conformation, it is probable that the C-helix which is not paired with the central trimer consisting of the N-helices adopts a free ("coil") conformation. In the open conformation according to the invention, the N-helices are paired with one another in the parallel orientation, preferably forming a trimer. In the case of the monomer, in the open conformation according to the invention, the C-helix is not paired with the N-helix.

The production of an open conformation can be demonstrated using the technique of measuring the intrinsic fluorescence of the polypeptide, as described by Schmid, F. X. (1989) "Spectral methods of characterising protein conformation and conformational changes" Creighton, T. E. Protein structure—a practical approach. pp251–284, IRL, Oxford University Press. In summary, the polypeptide will be excited at 295 nm and the fluorescence emission spectrum will be recorded at 310–380 nm. There is a correlation between the emission maximum of these wavelengths and the environment of the tryptophans in the structure. A tryptophan residue which is totally exposed to the solvent (i.e. a hydrophilic environment) has an emission maximum of approximately 355 nm, whereas a tryptophan residue which is protected from the solvent (i.e. present on the inside of the polypeptide) has an emission maximum of approximately 325 nm. In its trimeric form, the polypeptide according to the invention has 9 tryptophan residues at the N/C interfaces. The production of an open conformation will therefore result in an increase in the emission maximum recorded at 310–380 nm.

The polypeptide according to the invention has the particularity of being stable, i.e. it conserves it intermediate conformation under physiological conditions. The stability of the peptide according to the invention can easily be controlled using the differential scanning calorimetry (DSC) technique which is well known to those skilled in the art. Reference may be made, for example, to the articles by A. Cooper et al, Phil Trans. R. Soc. Lon. A (1993) 345, 23–25, and by V. V. Plotnikov et al. Analytical Biochemistry 250, 237–244 (1997).

The applicant has also surprisingly demonstrated that the open conformation of the polypeptide of the present invention is maintained in a strongly acid medium. The polypeptide of the present invention is thus particularly appropriate as an antigen usable in an oral vaccine. The applicant has indeed shown that gp41 ectodomain has a very high thermostability at pH=2.5 and that the polypeptide of the invention shows the same feature.

The polypeptide according to the invention consists of the sequence corresponding to the gp41 protein lacking all or part, preferably all, of the sequence corresponding to the transmembrane domain. The polypeptide according to the invention also lacks all or part, preferably all, of the sequence corresponding to the fusion peptide. According to a preferred embodiment, all or part of the sequence corresponding to the intracytoplasmic domain is also deleted.

In the context of the present invention, the term "gp41" is intended to mean a gp41 protein derived from any strain of HIV1 or of HIV2, preferably of HIV1, including laboratory strains and primary isolates. By way of illustration, mention may be made of MN and BX08 strains.

The nucleotide sequence and peptide sequence of a large number of gp41 proteins are known and available for example, over the internet or in the corresponding Los Alamos compendia. It is clear that any sequence into which one or more conservative mutations has been introduced is also included in the context of the present invention.

The various constituent domains of gp41, identified above, are defined herein with reference to the sequence of gp41 LAI as represented in FIG. 2, in which the $1^{st}$ amino acid A is numbered 1. Not all authors agree on the definition of the sequences corresponding to the fusion peptide and to the transmembrane domain. According to some authors, the fusion peptide corresponds to the sequence 1–32.

Although deletion of the sequence 1–23 is preferred, in particular because of the presence of a methionine at position 24, deletion of the sequence 1–32 is also suitable in the context of the present invention.

Regarding the transmembrane domain, some authors consider that the latter begins at residue 154. Although deletion of the sequence 173–194 is preferred, deletion of the sequence 154–194 is also envisaged in the context of the present invention.

The polypeptide according to the invention can be obtained by mutation of the natural sequence of gp41.

According to a preferred embodiment, the polypeptide according to the invention is prepared from the sequence of gp41 LAI in which the transmembrane domain and the fusion peptide, and also part of the intracytoplasmic domain, have been deleted. This sequence is represented in FIG. 3.

The mutations identified in the subsequent text are numbered with reference to the sequence in FIG. 3, in which the $1^{st}$ amino acid M is numbered 1.

The applicant has demonstrated a certain number of mutations which destabilize the structure of the latent state and/or of the fusogenic state of gp41 (in the monomeric and/or trimeric state) and/or stabilize the intermediate state of gp41 (in the monomeric and/or trimeric state), and/or promote the transconformation from the latent state to the intermediate state and/or hinder the transconformation from the intermediate state to the fusogenic state. These mutations make it possible to stabilize the polypeptide according to the invention in an open conformation.

The applicant has demonstrated that the polypeptide according to the present invention, and more particularly the N- and C-helices identified in the structure in the fusogenic state, may be divided into four regions (numbered with reference to the sequence of FIG. 3) corresponding, respectively, to the sequences Ala7-Ile25 (region 1), Glu26-Ala44 (region 2), Arg45-Leu58 (region 3) and Trp94-Lys131 (region 4), and that the mutations which modify the electrostatic properties and/or the amphilicity and/or the structural properties of these regions lead to the production of a polypeptide in the open conformation, according to the invention. The applicant has, in particular, shown that modifying the structure of region 2, changing from an extended structure to an α-helical structure, leads to the formation of the N-helix and the production of an open conformation.

The introduced modifications can be evaluated using conventional methods which are well known to those skilled in the art. By way of a method which may be used, mention may be made, for example, of the method of Eisenberg, which allows measurement of the mean-hydrophobicity and of the mean hydrophobic moment along the sequence; and the analysis of hydrophobic clusters, of molecular hydrophobicity potentials or of molecular electrostatic potentials. The structural modifications can be evaluated, for example, with studies of molecular dynamics and also with software for predicting secondary structures, such as PHD, NPSA, etc. These methods are described in the following articles: Method of Eisenberg: D., Schwarz, E., Komaromy, M. and Wall, R. 1984 *Journal of Molecular Biology,* 179:123–142; Analysis of hydrophobic clusters: Gaboriaud, C., Bissery, V., Benchetrit, T. and Mornon, J P. 1987, *FEBS Letters.* 224 (1): 149–55; Molecular Hydrophobicity Potential: Brasseur, R. 1991, *Journal of biological chemistry,* 266:16120–16127; Molecular Electrostatic Potential: Delleers, M. and Brasseur, R. 1989 *Biochemical Pharmacology,* 38 (15): 2441–2447; Molecular Dynamics (study of stability): Berendsen, H. J. C., van der Spoel, D. and van Drunen, R. 1995 GROMACS, *Computer Physics Communications,* 95:43–56; Molecular Dynamics (transconformation): Guilbert, C., Perahia, D. and Mouawad, L. 1995, *Computer Physics Communications,* 91:263–273; PHD: Rost, B. and Sander, C. 1994 *Proteins,* 19: 55–72; NPSA: Combet, C., Blanchet, C., Geourjon, C. and Deléage, G. 2000 *Trends in biochemical sciences,* 25 (3): 147–150.

The applicant has shown that the mutations as defined above which are related to the amino acids of region 1 hinder the interactions of this region with regions 3 and 4 in the latent state and/or with region 4 in the fusogenic state, and/or promote the multimerization of this region in the fusogenic state. The mutations as defined above which relate to the amino acids of region 2 promote an α-helical structure for this region and/or the transconformation to such a structure, and/or hinder the interactions of this region with regions 3 and 4 in the latent state and/or with region 4 in the fusogenic state, and/or promote the multimerization of this region in the fusogenic state. The mutations as defined above which relate to the amino acids of region 3 promote the multimerization in the latent state and/or in the fusogenic state, and/or hinder the interactions of this region with regions 1 and 2 in the latent state and/or with region 4 in the fusogenic state. The mutations as defined above which relate to the amino acids of region 4 promote the multimerization of this region in the latent state, and/or hinder the interactions with this region with regions 1 and 2 in the latent state and/or with regions 1, 2 or 3 in the fusogenic state.

Regions 1 to 4 of the polypeptide according to the invention and also the function of the mutations are summarized in FIGS. 4 and 5. In FIG. 4, regions 1 to 4 are located in the complete gp41 protein which, therefore, includes the fusion peptide (AA1–23) with the $1^{st}$ amino acid A numbered 1).

In the subsequent text, the amino acids are represented by their international code, and the code $L_1NNL_2$ indicates that the amino acid which is represented by $L_1$ and which is located at position NN is mutated at the amino acid represented by $L_2$.

The present invention thus provides a polypeptide comprising at least one mutation, preferably two mutations, selected in the group consisting of: T35I or L; V49I or L; Q56I or L; I101D or S; I108D and W94D. These mutations are preferably selected in the group consisting of T35I and I101D or S. This first mutation is preferably combined with at least one other mutation, preferably with 1 to 3 mutations, which are located preferably in at least of the regions 1 to 4. When two mutations are selected in the group identified above, these mutations are combined with at least one other mutation, preferably with 1 to 2 mutations, located preferably in at least of the regions 1 to 4.

The polypeptide according to the present invention preferably comprises at least two mutations which hinder the interactions between the N/C helices. According to a particularly preferred aspect, these two mutations are combined with at least one mutation, preferably at least two mutations, which promote the interactions between the N helices in a parallel orientation. The polypeptide thus obtained may also advantageously comprise one or more of the other mutations having the effects identified in FIG. 4 and in particular at least one of the mutations identified in table 1 in columns 3 to 6.

These additional mutations are preferably selected in the group comprising the following mutations: G13A, L, M, I, W or K; Q17A or E; Q18A or E; A24Q, E, S or R; Q28A; T35I or L; V36Q or E; W37S or D; G38A, V, L, I, M or E; Q39A, V, L, I, M or E; K40E, A, V, L, I or M; Q41A, V, L, I, M or E; Q43A, V, L, I, M or E; L47A or D; V49I or L; R51A, N or E; Q56I; C64S; C70S; or L; W94D; D98A, V, L, I, M or K; R99A, N or E; I101D or S; Y104M or E; I108D; Q119A, V, L, I, M, S, N or R; E120A; K121A; E123A; E125A; R153N or A et R173N or A.

Preferably, positions K40 and D98 are not simultaneously mutated.

Examples of combination of additional mutations which can be used in the present invention are: Q17A+Q18A; Q17A+Q18A+Q28A; Q41E+Q43E; C64S+C70S; E120A,+K121A; E120A+E123A and K121A+E125A.

According to a preferred embodiment, the polypeptide of the invention comprises the mutation(s): T35I; V49I; Q56I; T35I+Q28I+I101D; T35I+Q28I+I101D+Q119N; V49I+Q28I+I101D; V49I+Q28I+I101D+Q119N; Q56I+Q28I+I101D; Q56I+Q28I+I101D+Q119N; I101D; I101S; I108D; W94D; I101D+Q28I+V49I; I101D+Q281I+Q56I; I101S+Q28I+T35I; I101S+Q28I+V49I; I101S+Q28I+Q56I; I108D+Q28I+T35I; I108D+Q28I+V49I; I108D+Q28I+Q56I; W94D+Q28I+T35I; W94D+Q28I+V49I; W94D+Q28I+Q56I; I101D+I108D+Q131N+W37A; I101S+I108D+Q131N+W37A; W94D+I108D+Q131N+W37A; I101D+W94D+Q131N+W37A; I101S+W94D+Q131N+W37A; I101D+I108D+Q142N+L126D; I101S+I108D+Q142N+L126D; W94D+I108D+Q142N+L126D; I101D+W94D+Q142N+L126D; I101S+W94D+Q142N+L126D; T35I+Q28I+I101S+Q119N; V49I+Q28I+I101S+Q119N; Q56I+Q28I+I101S+Q119N; T35I+Q28I+I108D+Q119N; V49I+Q28I+I108D+Q119N; Q56I+Q28I+I108D+Q119N; T35I+Q28I+W94D+Q119N; V49I+Q28I+W94D+Q119N; Q56I+Q28I+W94D+Q119N; T35L; V49L; Q56L; T35L+Q28I+I101D; T35L+Q28I+I101D+Q119N; V49L+Q28I+I101D; V49L+Q28I+I101D+Q119N; Q56L+Q28I+I101D; Q56L+Q28I+I101D+Q119N; I101D+Q28I+following V49L; I101D+Q28I+Q56L; I101S+Q28I+T35L; I101S+Q28I+V49L; I101S+Q28I+Q56L; I108D+Q28I+T35L; I108D+Q28I+V49L; I108D+Q28I+Q56L; W94D+Q28I+T35L; W94D+Q28I+V49L; W94D+Q28I+Q56L; T35L+Q28I+I101S+Q119N; V49L+Q28I+I101S+Q119N; Q56L+Q28I+I101S+Q119N; T35L+Q28I+I108D+Q119N; V49L+Q28I+I108D+Q119N; Q56L+Q28I+I108D+Q119N; T35L+Q28I+W94D+Q119N; V49L+Q28I+W94D+Q119N; or Q56L+Q28I+W94D+Q119N; W37A+I101D+I108D+Q119N or I101D+I108D+Q119N+L126D.

These polypeptides preferably correspond to a polypeptide of sequence SEQ ID NO 2 in which the above-mentioned mutations have been introduced.

Examples of polypeptides of the present invention which are particularly preferred are polypeptides of sequence SEQ ID NO 2 in which the following mutation(s) have been introduced: T35I; I101D; T35I+Q28I+I101D; T35I+Q28I+I101D+Q119N; I101D+I108D+Q131N+W37A or I101D+I108D+Q142N+L126D; W37A+I101D+I108D+Q119N or I101D+I108D+Q119N+L126D.

Other modifications may be introduced into the polypeptide of the invention, for example in order to facilitate expression and promote better solubility. Advantageously, one or both cysteine at position 64 and position 69 may be replaced, for example, with serine.

Although the polypeptide according to the invention has an open conformation which is stable under physiological conditions, this conformation can be reinforced by adding cysteine residues to the ends of the polypeptide. To this end, two additional cysteine residues can be added at the N-terminal or at the C-terminal, preferably at the N-terminal, of the polypeptide according to the invention so as to covalently fix the trimer in an open conformation. In this case, the amino acids Q17 and Q18 are preferably mutated to cysteine.

The mutations proposed may be combined in order to obtain a synergistic effect or, at the very least an additive effect. The polypeptide according to the present invention preferably comprises at least two mutations which hinder the interactions between the N/C helices. According to a particularly preferred aspect, these two mutations are combined with at least one mutation, preferably at least two mutations, which promote the interactions between the N helices in a parallel orientation. The said polypeptide thus obtained may also advantageously comprise one or more of the other mutations having the effects identified in FIG. 4 and in particular at least one of the mutations identified in Table 1 in columns 3 to 6.

The mutations proposed in the context of the present invention are summarized in Table 1.

Dawson P E et al Synthesis of native proteins by chemical ligation, Annu Rev Biochem 2000;69:923–60.

The polypeptide according to the invention can also be produced using genetic engineering techniques which are well known to those skilled in the art. These techniques are described in detail in Molecular Cloning: a molecular manual, by Maniatis et al. (Cold Spring Harbor, 1989). Conventionally, the DNA sequence encoding the polypeptide according to the invention is inserted into an expression vector, which is mutated by site-directed mutagenesis. When

TABLE 1

| | | Functions | | | | | |
|---|---|---|---|---|---|---|---|
| | | 1 Hinder the interactions between the N- and c-helices in the fusogenic state | 2 Promote the interactions between the N- helices in the fusogenic state | 3 Promote and α- helical structure | 4 Hinder the interactions between regions 2 and 3 in the latent state | 5 Hinder a loop structure in region 2 | 6 Eliminate a potential area of interaction |
| Initial AA/position | Mutation | | | | | | |
| G13 | A, L, M, I W or K | x | | x | | | |
| Q17 | A or E | x | | | | | |
| Q18 | A or E | | x | | | | |
| A24 | Q, E, S or R | x | | x | | | |
| Q28 | A | | x | | | | |
| T35 | L or I | | x | | | | |
| V36 | Q or E | x | | x | | | |
| G38 | A, V, L, I, E or M | x | | x | | | |
| K40 | E, A, V, L, I or M | x | | | | | |
| D98 | A, V, L, I, M or K | x | | | | | |
| Q39 | A, V, L, I, M or E | | | | | x | |
| Q41 | A, V, L, I, M or E | | | | | x | |
| Q43 | A, V, L, I, M or E | x | | | | x | |
| L47 | A or D | | | | x | | |
| V49 | I or L | | x | | | | |
| R51 | A, N or E | | | | x | | |
| Q56 | L or I | | x | | | | |
| C64 | S | | | | | | x |
| C70 | S | | | | | | x |
| W94 | D | x | | | | | |
| D98 | A, L, V, I, M or K | x | | | | | |
| R99 | A, N or E | x | | | | | |
| I101 | D or S | x | | | | | |
| Y104 | M or E | x | | | | | |
| I108 | D | x | | | | | |
| Q119 | A, V, L, I, M S or R | x | | | | | |
| E120 | A | | | | | | x |
| K121 | A | | | | | | x |
| E123 | A | | | | | | x |
| E125 | A | | | | | | x |
| W37 | S or D | x | | | | | |
| R153 | N or A | | | | | | x |
| R173 | N or A | | | | | | x |

The polypeptide according to the invention can be obtained using any conventional technique of chemical synthesis or of genetic engineering.

When the polypeptide is produced by chemical synthesis, the polypeptide according to the invention can be synthesized even in the form of a single sequence or in the form of several sequences which are then attached to one another. The chemical synthesis can be carried out in solid phase or in solution, these two techniques for synthesis being well known to those skilled in the art. These techniques are in particular described by Atherton and Shepard in "solid phase peptide synthesis" (IRL press Oxford, 1989) and by Houbenweyl in "method der organischen chemie" edited by E. Wunsch vol, 15-I and II thieme, Stuttgart, 1974, and also in the following articles: Dawson P E et al (Synthesis of proteins by native chemical ligation Science 1994;266 (5186): 776–9); Kochendoerfer G G et al (Chemical protein synthesis. Curr Opin Chem Biol 1999;3(6): 665–71); and several mutations must be introduced, a first mutagenesis reaction is carried out and then the resulting mutated plasmid is used as a matrix for carrying out the second mutagenesis reaction in order to obtain the plasmid comprising the double mutation. When two mutations are separated by less than 5 amino acids, these two mutations are carried out simultaneously with a single oligonucleotide which carries the two mutations.

The expression vector containing the mutated sequence is then used to transform a host cell which allows expression of the sequence of interest. The polypeptide produced is then isolated from the culture medium using conventional techniques which are well known to those skilled in the art, such as ethanol precipitation or ammonium sulfate precipitation, acid extraction, anion/cation exchange chromatography, phosphocellulose chromatography, hydrophobic interaction chromatography, affinity chromatography, hydroxyapatite chromatography and lectin chromatography. Preferably, high performance liquid chromatography (HPLC) is used in the purification.

The purified polypeptide may be in various forms depending on the expression system used (secreted or non-secreted protein) and the purification process. It may be in a denatured or nondenatured, monomeric or multimeric form. When it is in a denatured form, it is possible to return it to its open conformation according to the invention using the process described in Example 1. In order to obtain multimeric forms and in particular trimers, the purified polypeptide molecules must be placed in a medium in which the molecules are completely soluble, have no interactions with one another and preferably have no secondary structure. For this, detergents such as sodium dodecyl sulfate, N lauryl sarcosine, guanidinium chloride, urea, sodium thiocyanate or chaotropic agents may be used. The desired conditions may be promoted by using organic solvents or acids. Once this first condition is satisfied, the sample is placed in a dialysis cassette in order to remove some of the chaotropic agents, in such a way as to promote the interactions between the polypeptide monomers while maintaining sufficient solubility for the molecules. In a second step, the formation of the trimers having been promoted, the sample is thoroughly dialyzed in a physiological medium which maintains the polypeptide solution or in suspension. Trimers of the polypeptide according to the invention, in an open conformation, are then obtained. Such a technique is described in detail in WO 00/08167.

Any expression vector conventionally used for expressing a recombinant protein may be used in the context of the present invention. This term therefore encompasses both "living" expression vectors, such as viruses and bacteria, and expression vectors of the plasmid type.

Use is preferably made of vectors in which the DNA sequence of the polypeptide according to the invention is under the control of a strong promoter which may be inducible or noninducible. By way of example of a promoter which may be used, mention may be made of the T7 RNA polymeraze promoter.

The expression vectors preferably include at least one selection marker. Such markers include, for example, dihydrofolate reductase or neomycin resistance, for culturing eukaryotic cells, and kanamycin, tetracycline or ampicillin resistance genes for culturing in E. coli and other bacteria.

By way of an expression vector which may be used in the context of the present invention, mention may be made of the plasmids pET28 (Novagen) or pBAD (Invitrogen) for example; and viral vectors such as: baculoviruses, pox viruses, in particular the pox viruses described in U.S. Pat. Nos. 5,942,235, 5,756,103 and 5,990,091, or recombinant vaccinia viruses, in particular the recombinant viruses described in patents EP 83286, U.S. Pat. No. 5,494,807 and U.S. Pat. No. 5,762,938.

The site-directed mutagenesis is carried out according to the conventional techniques commonly employed by those skilled in the art, for example using the Pfu polymerase (Quick Change Mutagenesis Kit, Stratagene) or the bio rad mutagenesis kit. The mutations are confirmed by sequencing in the usual manner. This type of method is described in detail in Maniatis et al. (Molecular cloning, a laboratory manual, cf. above).

In order to promote the expression and purification of the polypeptide, the latter may be expressed in a modified form, such as a fusion protein, and may include not only secretion signals but also additional heterologous functional regions. For example, a region containing additional amino acids, particularly charged amino acids, may be added to the N-terminal of the polypeptide in order to improve stability and persistence in the host cell.

Any host cell conventionally used in combination with the expression vectors described above may be used for the expression of the polypeptide.

By way of nonlimiting example, mention may be made of the E. coli cells BL21 (λDE3), HB101, Top 10, CAG 1139, Bacillus and eukaryotic cells such as CHO or Vero.

In the context of the present invention, the following expression vector/cell system: pET(Cer)/BL21LamdaDE3 or BL21lamdaDE3(RIL) will preferably be used.

The polypeptides of the present invention may be glycosylated or nonglycosylated, depending on the host employed in the procedure for production via the recombinant pathway. In addition, the polypeptides of the invention may also include an additional N-terminal methionine residue.

A subject of the present invention is also the conjugates comprising a polypeptide according to the invention and a carrier protein or a carrier peptide. The carrier protein (or peptide) reinforces the immunogenicity of the polypeptide according to the invention, in particular by increasing the production of specific antibodies. Said carrier protein (or peptide) preferably comprises one or more helper-T epitope (s). The term "helper-T epitope" is intended to mean an amino acid chain which, in the context of one or more class II MHC molecules, activates helper T lymphocytes. According to an advantageous embodiment, the carrier protein (or peptide) used improves the water-solubility of the polypeptide according to the invention.

As a carrier protein, use may be made, for example, of phage surface proteins, such as the pIII or pVIII of the protein M13 phage, bacterial surface proteins, such as the LamB, OmpC, ompA, ompF and PhoE proteins of E. coli, the CotC or CotD protein of B. Subtilis, bacterial porines, such as porine P1 of Neisseria gonorrheae, porine P1 or P2 of H. influenzae B, the class I porine of N. meningitidis B or porine P40 of K. pneumoniae, lipoproteins, such as OspA of B. bugdorfi, PspA of S. pneumoniae, TBP2 of N. meningitidis B, TraT of E. coli and also adhesin A of S. pneumoniae, and the heat shock proteins, such as Hsp65 or Hsp71 of M. tuberculosis or bovis, or Hin 47 of H. influenzae type B. Detoxified bacterial toxins, such as tetanus or diphtheria toxoid, the B subunit of cholera toxin, or the B subunit of endotoxin A of P. aeruginosa or exotoxin A of S. aureus, are also particularly suitable in the context of the present invention.

In the context of the present invention, carrier peptides which may be used include, for example, the p24E, p24N, p24H and p24M peptides described in WO 94/29339, and also the PADRE peptides as described by Del guercio et al (Vaccine (1997); vol 15/4, p441–448).

The carrier protein (or peptide) is linked to the N- or C-terminal end of the polypeptide according to the invention using any conjugation process which is well known to those skilled in the art. In addition, the sequence encoding the carrier protein (or peptide) may advantageously be fused to the sequence encoding the polypeptide according to the invention, and the resulting sequence may be expressed in the form of a fusion protein using any conventional process. All the genetic engineering techniques which can be used to do this are described in Maniatis et al. Said conjugates can be isolated using any conventional purification process which is well known to those skilled in the art.

A subject of the present invention is also the DNA sequences encoding the polypeptides and the conjugates according to the invention, and also the expression vectors comprising said sequences and the host cells transformed with said vectors.

Rather than extracting and purifying the polypeptide or the conjugate expressed by the expression vector, it is often easier and sometimes more advantageous to use the expression vector itself in the vaccine according to the invention. A subject of the present invention is therefore also any expression vector as defined above.

A host cell as defined above which is transformed with such an expression vector is included in the context of the present invention.

A subject of the present invention is also the antibodies directed against the polypeptides and conjugates as described above. Such antibodies are prepared using the conventional techniques for producing polyclonal and monoclonal antibodies, which are well known to those skilled in the art.

These antibodies are particularly suitable for use in a passive immunization scheme.

A subject of the present invention is also vaccines which can be used for therapeutic and prophylactic purposes. The vaccines according to the present invention comprise at least one polypeptide, at least one conjugate or at least one expression vector as defined above, a pharmaceutically acceptable support or diluent and, optionally, an adjuvant.

The amount of polypeptide, conjugate or of vector in the vaccine according to the present invention depends on many parameters, as will be understood by those skilled in the art, such as the nature of the carrier protein, the vector used or the route of administration. A suitable amount is an amount such that a humoral immune response capable of neutralizing primary isolates of HIV is induced after administration of the latter. The amount of polypeptide to be administered is about 10 to 100 micrograms. The amount of conjugate to be administered will be deduced from the amounts indicated above, taking into account the MW of the carrier protein. The amount of expression vector to be administered is about 10 to 5000 micrograms in the case of a nonviral vector and about $10^E4$ to $10^E8$ TCID50 in the case of a viral vector.

The vaccines according to the present invention may also contain an adjuvant. Any pharmaceutically acceptable adjuvant or mixture of adjuvants may be used for this purpose. By way of example, mention may be made of aluminum salts, such as aluminum hydroxide or aluminum phosphate. Conventional auxiliary agents, such as wetting agents, fillers, emulsifiers, buffers etc., may also be added to the vaccine according to the invention.

The vaccines according to the present invention can be prepared using any conventional process which is known to those skilled in the art. Conventionally, the antigens according to the invention are mixed with a pharmaceutically acceptable support or diluent, such as water or phosphate buffered saline solution. The support or diluent will be selected as a function of the pharmaceutical form chosen, of the mode and route of administration and of pharmaceutical practice. Suitable supports or diluents and the requirements concerning pharmaceutical formulation are described in detail in Remington's Pharmaceutical Sciences, which represents a reference work in this field.

The vaccines mentioned above may be administered by any conventional route normally used in the field of vaccines, such as the parenteral (intravenous, intramuscular, subcutaneous, etc.) route. In the context of the present invention, intramuscular administration will preferably be used. Such an administration can advantageously be carried out in the muscles of the thigh or of the arm. Administration via the nasal, oral, vaginal or rectal mucous membrane route may also be recommended in the context of the present invention. The administration can be carried out by administering a single dose or repeat doses, for example on D0, at 1 month, at 3 months, at 6 months and at 12 months. Injections on D0, at 1 month and at 3 months, with a booster, the frequency of which may be easily determined by the treating physician, will preferably be used.

The vaccine according to the present invention may advantageously be administered according to a posology scheme comprising the co-administration of an expression vector according to the invention and of a polypeptide according to the invention, or according to a prime-boost scheme in which the vector according to the invention is administered first and the polypeptide is administered as a booster injection. In these two posology schemes, the expression vector according to the invention may be replaced with any expression vector expressing one or more HIV antigens or epitopes other than the polypeptide according to the invention, and in particular with an ALVAC or NYVAC vector.

The present invention is also understood to cover a polypeptide, conjugate or a vector as defined above and the vaccine containing these compounds, for their use in inducing antibodies which neutralize primary isolates of HIV.

The applicant has demonstrated, surprisingly, that the polypeptide according to the invention is capable, after administration, of inducing antibodies which are capable of neutralizing primary isolates of HIV. These antigens therefore represent valuable candidates for developing a vaccine which can be used for the protection and/or treatment of a great number, or even all, of the individuals at risk or infected with HIV.

The present invention therefore also relates to a method for inducing an immune response in a host individual, including humans, comprising the administration of a vaccine according to the invention. The term "an immune response" is intended to mean a response comprising the production of antibodies directed specifically against the polypeptide according to the invention. The production of specific antibodies can be easily determined using conventional techniques which are well known to those skilled in the art, such as ELISA, IRA or Western blot. The present invention thus also provides a method of induction of antibodies neutralizing HIV comprising administratioon to a mammal of an efficient amount of a polypeptide of the invention. An efficient amount is an amount which is sufficient to induce the formation of neutralizing antibodies. The person ssskilled in the art can easily determined the amount appropriate for each patient.

A subject of the invention is also a diagnostic method comprising bringing a polypeptide according to the invention into contact with a biological sample and detecting the antibody/polypeptide complexes formed.

The polypeptide of the present invention can indeed be used in ELISA assays to detect anti-gp41 antibodies present in the serum of patients. The polypeptide of the present invention is thus useful as a diagnostic tool since the presence of anti-gp41 antibodies is a reliable marker of an HIV infection.

In such a case the polypeptide of the invention is coated on an ELISA plate, contacted with serial dilutions of the patient serum to be tested and then contacted with a enzyme-linked anti-human antibody. The anti-human antibody/anti-gp41 antibody/polypeptide complex thus formed is then detected by colorimetric detection.

The present invention will be described in greater detail in the examples which follow, with reference to the attached figures in which:

FIG. 1 is a schematic representation of the phenomenon of conformational change of gp41 which precedes the fusion of the cell and viral membranes.

FIG. 2 gives the complete sequence of gp41 LAI in which (_____) represents the fusion peptide and (------) represents the transmembrane domaine.

FIG. 3 gives the sequence of the polypeptide which derives from the gp41 LAI protein which is used as the starting product in the examples provided.

Figure 5:
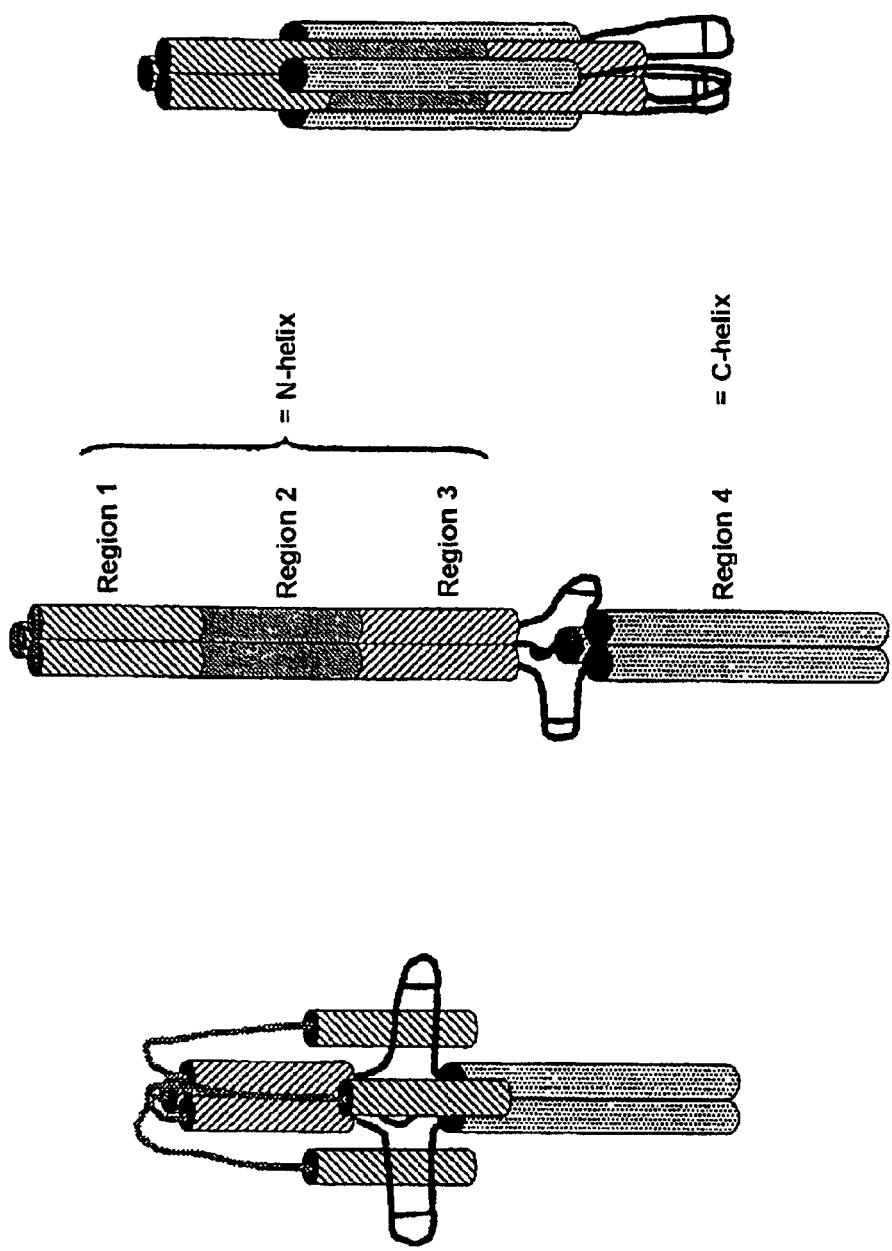

FIGS. 4 and 5 give a schematic representation of regions 1 to 4; FIG. 4 summarizes the functions of the mutations envisaged. The numbers given between brackets refer to the regions identified, "promote the interactions (3–12)" meaning that the interactions between region 3 and regions 1 and 2 are promoted.

The examples described below are given purely by way of illustration of the invention and cannot in any way be considered as limiting the scope of the latter.

EXAMPLE 1

Preparation of Various Polypeptides According to the Invention

1—Cloning the Sequence of FIG. 3 Into an Expression Vector

The DNA sequence encoding the polypeptide identified in FIG. 3 was cloned into an inducible expression system.

The vector used is pET-CER, which is constructed from the vector pET28 from Novagen. The commercial vector pET28c was amplified by PCR using 2 primers located on either side of the region corresponding to the origin F1, in such a way that the amplified product corresponds to virtually the entire vector of origin, less the region comprising the origin F1. The unique AscI and PacdI restriction sites are provided, respectively, by the two primers which have been used for the amplification. In parallel, the CER fragment is amplified using two primers which make it possible to obtain this fragment bordered by AscI and PacdI sites.

The CER fragment and vector are digested with the AscI and PacdI enzymes and then ligated to one another. This vector in particular comprises an expression cassette under the control of the T7 promoter, a polylinker downstream of the T7 promoter, for cloning the gene of interest, the CER fragment located downstream of the polylinker, making it possible to decrease the multimerization of the plasmids, a T7 term transcription terminator and the kanamycin resistance gene.

Positive regulation of the promoter is obtained in the presence of T7 RNA polymeraze.

2—Site-Directed Mutagenesis

The site-directed mutagenesis for producing the mutated polypeptides according to the invention is carried out using the QuickChange site-directed mutagenesis kit from Stratagene.

For each mutation, two mutagenesis oligonucleotides which border the amino acid to be mutated are defined. For example, for the R51A mutation, the following oligonucleotides are used:

```
                              R
Reference        ctg gct gtg gaa aga tac cta aag gat
sequence A
5' oligonucle-   ctg gct gtg gaa gca tac cta aag gat
otide 3' oligonucle-   atc ctt tag gta tgc ttc cac agc cag
otide
```

The 2 oligonucleotides will hybridize to the same sequence on the complementary strands of the plasmid containing the sequence to be mutated. The mutation is located at the center of the oligonucleotides and it is bordered by 12 nucleotides on each side.

The mutagenesis reaction is carried out on the plasmid of Example 1 under the following conditions: a mixture containing: 5 µl 10× reaction buffer; 1 µl plasmid to be mutated, 100 ng/µl; 1 µl 5'Oligo (125 ng/µl); 1 µl 3'Oligo (125 ng/µl); 1 µl 10 mM dNTP Mix; 40 µl UF H$_2$O; and 1 µl *Pyrococcus furiosus* heat-stable polymeraze, 2.5 U/µL, is subjected to a PCR according to the cycles defined below: 95° C., 30"; 95° C., 30"; 55° C., 1'; 68° C., 2'/kpb of plasmid; 12 cycles; temperatures at the end of the reaction: 20° C.

Using the protocol above, the various mutants identified in Table 1 were prepared.

3—Expression

The expression of the plasmids derived from step 2 above is carried out in *E. coli*.

To do this, a modified *E. coli* strain is used: BL21 IRLλDE3.

This strain is enriched in rare tRNAs (ARG, ILE, LEU); it contains the gene encoding T7 RNA polymerase, which gene is under the control of the lac UV5 promoter which can be induced by adding IPTG at a concentration of 1 mM. Initially, the strain is transformed with the mutated plasmid according to the protocol comprising the following steps: 3 colonies are subcultured in 10 ml of LB+ANTIBIOTIC; they are incubated overnight at 37° C.; the preculture is re-seeded at 1:100 in 15 ml of LB+ANTIBIOTIC; it is allowed to grow until an OD600 of 0.5 is obtained; 1 ml is removed in order to verify the OD600; 7 ml are removed for the noninduced sample; the other 7 ml are induced with 1 mM of IPTG and induction carried out for 3H at 37° C.

The same protocol was carried out on several liters of culture in order to produce a large amount of bacteria for purifying the mutated polypeptide.

4—Purification

The cell pellet made up of the bacteria harvested from one liter of culture medium is thawed and taken up in 2×100 ml of 30 mM Tris buffer at pH8 in the presence of a protease inhibitor (Pefabloc, Interchim) at a concentration of 100 µM. Lysozyme is added at the concentration of 100 µg/ml and the mixture is incubated for 30 minutes at room temperature. The cells are then ruptured by sonication (4 cycles of two minutes) with an approximate power of 150 watts. The gp41 is in the form of inclusion bodies. They are washed in a PBS-0.05% tween 20 buffer at 4° C. and centrifuged for 15 minutes at 10,000 g. After removing the supernatant, the centrifugation pellet composed essentially of the inclusion bodies is solubilized over one hour at room temperature with gentle stirring in the presence of 50 ml of CAPS buffer at pH 10.4 containing 3% of N-lauryl sarcosine.

The solubilized fraction is then dialyzed at 4° C. against a 30 mM Tris buffer at pH 8 containing 8 M urea (5 bars), filtered through a filter with a porosity of 0.45 μm and then loaded onto a 1 ml high Hi-Trap column (Pharmacia). These affinity chromatography supports chelate nickel atoms to which the histidine residues of the C-terminal end of the protein attach.

After washing, the protein is eluted in the 30 mM Tris buffer at pH 8 containing 8M urea and 500 mM imidazole. The eluted fractions are dialyzed in a 30 mM Tris buffer at pH8 containing 8M urea, but with no imidazole, and with decreasing amounts of urea, ranging down to 2M. This technique makes it possible to purify all the mutant or native gp41 molecules in the presence or absence of the fusion peptide.

EXAMPLE 2

Immunogenicity and Induction of Neutralizing Antibodies

The tested immunogen corresponds to the polypeptide according to the present invention of sequence SEQ ID NO2 in which the I101D mutation has been introduced by directed mutagenesis and which comprises a C terminal HIS tag sequence in order to facilitate the purification. Preparation of the immunogen was done according to the processes described in the preceding examples.

Groups of 5 guinea-pigs were immunized 3 times by the intramuscular route (into the thigh, in the biceps femoris muscle) at 3 week intervals (days 1, 22 and 43) with 20 μg per dose of either native gp41 or polypeptide I101D in the presence of 6 mg of aluminium phosphate. The immunogen was administered under a volume of 0.5 ml, ie 0.25 ml in each thigh. Serum samples were taken at D1, D43 and D57. Individual immune sera (D43) and pools per group of preimmune sera (D1) were tested by ELISA for their IgG antibody titers induced against native gp41 and gp 160 MN/LAI-2.

Individual immune sera (D57) and pools of 2 groups of preimmune sera (D1) were evaluated for their seroneutralizing activity against primary HIV-1 isolate Bx08.

The results thus obtained clearly demonstrated that the polypeptide of the invention is as immunogen as the native gp41. Furthermore, the neutralization assay of C. Moog et al has shown that the polypeptide of the invention induces neutralizing antibodies (% of reduction>of a factor 10).

What is claimed is:

1. A mutated gp41 polypeptide capable of forming a structure corresponding to or mimicking the intermediate state of gp41 comprising at least one mutation selected in the group consisting of T35I or L; W49I or L; Q56I or L; I101D or S; I108D and W94D.

2. The polypeptide according to claim 1 comprising at least a second mutation selected in the group consisting of G13A, L, M, I, W or K; Q17A or E; Q18A or E; A24Q, E, S or R; Q28A; T35I or L; V36Q or E; W37S or D; G38A, V, L, I, M or E; Q39A, V, L, I, M or E; K40E, A, V, L, I or M; Q41A, V, L, I, M or E; Q43A, V, L, I, M or E; L47A or D; V49I or L; R51A, N or E; Q56I; C64S; C70S or L; W94D; D98A, V, L, I, M or K; R99A, N or E; I101D or S; Y104M or E; I108D; Q119A, V, L, I, M, S, N or R; E120A; K121A; E123A; E125A; R153N or A; and R173N or A.

3. The polypeptide according to claim 1 comprising the following mutations: T35I; I101D; T35I+Q28I+I110D; T35I+Q28I+I101D+Q119N; I101D+I108D+Q131N+W37A; I101D+I108D+Q142N+L126D; W37A+I101D+I108D+Q119N or I101D+I108D+Q119N+L126D.

4. The polypeptide having the SEQ ID No 2 sequence wherein at least one of the mutations defined in claim 1 has been introduced.

5. A conjugate comprising a polypeptide as claimed in claim 1, conjugated to a carrier protein or peptide.

6. A DNA sequence encoding a polypeptide as claimed in claim 1.

7. A DNA sequence encoding a conjugate as claimed in claim 5.

8. An expression vector comprising the DNA sequence as claimed in claim 6.

9. An expression vector comprising the DNA sequence as claimed in claim 7.

10. A host cell containing the vector as claimed in claim 8.

11. A host cell containing the vector as claimed in claim 9.

12. A process for preparing a polypeptide as claimed in claim 1, comprising the expression of said polypeptide using a host cell containing a vector comprising a DNA sequence encoding the polypeptide.

13. An antigenic composition comprising at least one polypeptide as claimed in claim 1, a pharmaceutically acceptable support and, optionally, an adjuvant.

14. An antigenic composition comprising at least one conjugate as claimed in claim 5, a pharmaceutically acceptable support and, optionally, an adjuvant.

15. An antigenic composition comprising at least one expression vector as claimed in claim 8, a pharmaceutically acceptable support and, optionally, an adjuvant.

16. A method of induction of antibodies against HIV comprising administration to a mammal of an efficient amount of a polypeptide according to claim 1.

* * * * *

UNITED STATES PATENT AND TRADEMARK OFFICE
CERTIFICATE OF CORRECTION

PATENT NO. : 6,861,253 B2
DATED : March 1, 2005
INVENTOR(S) : Robert Brasseur et al.

It is certified that error appears in the above-identified patent and that said Letters Patent is hereby corrected as shown below:

<u>Title page,</u>
Item [*] Notice, should read as follows:
-- Notice: Subject to any disclaimer, the term of this
Patent is extended or adjusted under 35 U.S.C. 154(b) by
313. --.

Signed and Sealed this

Twenty-ninth Day of November, 2005

JON W. DUDAS
*Director of the United States Patent and Trademark Office*